US007363239B1

(12) United States Patent
Andersson et al.

(10) Patent No.: US 7,363,239 B1
(45) Date of Patent: Apr. 22, 2008

(54) ARRANGEMENT FOR PRODUCING COMPLETE OR PARTIAL DENTAL PRODUCTS

(75) Inventors: Matts Andersson, Lerum (SE); Anders Tornquist, Partille (SE)

(73) Assignee: Nobel Biocare AB, Göeborg (SE)

( * ) Notice: Subject to any disclaimer, the term of this patent is extended or adjusted under 35 U.S.C. 154(b) by 1084 days.

(21) Appl. No.: 10/130,601

(22) PCT Filed: Nov. 8, 2000

(86) PCT No.: PCT/SE00/02181

§ 371 (c)(1),
(2), (4) Date: May 21, 2002

(87) PCT Pub. No.: WO01/37757

PCT Pub. Date: May 31, 2001

(30) Foreign Application Priority Data

Nov. 26, 1999   (SE) ..................... 9904276

(51) Int. Cl.
G06Q 10/00    (2006.01)
G06Q 50/00    (2006.01)

(52) U.S. Cl. .................. 705/2; 705/3; 705/7; 433/223; 106/35; 700/1

(58) Field of Classification Search .............. 705/2–3, 705/7; 433/223; 106/35; 700/1
See application file for complete search history.

(56) References Cited

U.S. PATENT DOCUMENTS

| | | | | |
|---|---|---|---|---|
| 4,799,887 A | * | 1/1989 | Hakamatsuka et al. | 433/212.1 |
| 5,616,899 A | * | 4/1997 | Recigno | 235/375 |
| 6,283,761 B1 | * | 9/2001 | Joao | 434/236 |
| 6,354,836 B1 | * | 3/2002 | Panzera et al. | 433/215 |
| 6,431,871 B1 | * | 8/2002 | Luthardt | 433/223 |
| 6,575,751 B1 | * | 6/2003 | Lehmann et al. | 433/223 |
| 7,107,226 B1 | * | 9/2006 | Cassidy et al. | 705/26 |
| 2002/0018981 A1 | * | 2/2002 | Andersson et al. | 433/223 |
| 2002/0172911 A1 | * | 11/2002 | Cooper | 433/24 |
| 2005/0010450 A1 | * | 1/2005 | Hultgren et al. | 705/3 |

FOREIGN PATENT DOCUMENTS

WO    9844865    10/1998

OTHER PUBLICATIONS

Gayle Geis O'Dowd. "High Tech Teeth" Oct. 4, 1999. Albuquerque Journal. p. C.1.*

(Continued)

*Primary Examiner*—C. Luke Gilligan
*Assistant Examiner*—Mike Tomaszewski
(74) *Attorney, Agent, or Firm*—Venable LLP; Eric J. Franklin

(57) ABSTRACT

An arrangement for producing at least a part of a dental product including an interface configured to receive and transmit ordering and manufacturing data from a plurality of users of different dental treatment systems. Ordering, manufacturing, and quality operating principles distinguish products from the different dental treatment systems to permit the arrangement to cooperate with the different dental treatment systems. At least one coordinating adapter unit receives and transmits ordering and manufacturing data from the different dental treatment systems. The at least one coordinating adapter unit identifies from which dental treatment system the ordering and manufacturing data comes and converts ordering and manufacturing data from at least one of the different dental treatment system to conform to another of the dental treatment systems. A communications network permits communication among elements of the system. Production units manufacture the dental product utilizing adapted manufacturing data.

27 Claims, 2 Drawing Sheets

OTHER PUBLICATIONS

Edward McDowell and Sabah Randhawa. "Dental Equipment Maker Uses Microcomputer-Based Data Management And Production Planning System" Jan. 1989. Industrial Engineering. vol. 21, Iss. 1. p. 24.*

Claudia Coplon. "Dental-Office Purchasing plus Internet equals Time- and Cost-Savings" Nov. 1998. Dental Economics. vol. 88, Iss. 11. p. 82.*

PR Newswire. "Lancer Orthodontics Introduces New Internet Ordering System for its Products" Nov. 24, 1998. p. 1.*

* cited by examiner

ARRANGEMENT FOR PRODUCING COMPLETE OR PARTIAL DENTAL PRODUCTS

TECHNICAL FIELD

The present invention relates to an arrangement included in or forming a system by means of which complete or partial dental products can be produced. The arrangement operates with principles for ordering, manufacturing and/or quality which distinguish the products or the partial products belonging to one of several different dental treatment systems available.

One example of a dental treatment system is the so-called Brånemark® system. Products and partial products in this are manufactured preferably using the PROCERA® system which is distinguished by rapid, high-quality and IT-controlled manufacture. Other systems of variable quality and manufacturing principles are available on the market.

PRIOR ART

Regarding the said manufacturing method which is based on PROCERA®, we refer inter alia to Swedish Patent 9701309-8 from the same Applicant. The patent specification in question discloses in detail an arrangement and system for dental product manufacture and information transmission. This system is today tailored to its own products, and only customers and markets subscribing to the PROCERA® system have in principle access to the products and partial products which are produced by this system.

As has been indicated above, there are a number of other systems on the market which are in turn tailored to their respective customer bases.

DISCLOSURE OF THE INVENTION

Technical Problem

Fully or partly mechanized production of dental products and partial products is characterized by increasingly advanced technology demanding considerable mechanical resources and substantial economic investment. The manufacturing is in principle computer-based and IT techniques are used, and information between dentist/dental technician and centralized manufacturing locations takes place via the telephone and/or computer network, in which case the Internet and/or the so-called IBM net is included or forms the communication links in question. The dentist or dental technician linked to the system can set out his requirements in situ and send order and query profiles via the said links to one or more central units which are specialized in the production of the products or partial products concerned. In connection with the production of dental products or partial products, there is a need to be able to widen the manufacture and involve customers who are not themselves linked up to the system's method for production. There is therefore a need to be able to use the advanced system (e.g. PROCERA®), which is used for production of the said qualified products, to include also those customers, i.e. dentists and/or dental technicians, who are not linked up to the actual system. There is therefore a need to allow customers access to all or part of the advanced system despite the fact that the persons or companies in question are not linked to the system as such. The main object of the invention is to solve this set of problems, inter alia.

In this connection it is known that the quality and structure of the dental products or partial products in question can vary considerably. The advanced system (PROCERA®) must be able to be used effectively in whole or in part and there is therefore a need for the advanced system to have activity and reception ability also in respect of other existing dental treatment systems. The invention solves this problem too.

The advanced system also includes payment functions which keep track of how the system's own customers are using the system in question so that debiting can take place on an economic basis. It is important in this case that the advanced system can also keep track of outside subscribers and customers with regard to their use of the system's services and contents. The invention solves this problem too.

In the manufacture of dental products or parts of such products, e.g. dental caps made of ceramic powder, it is important for the advanced system to be able to provide products of qualities and structures which are representative of the different dental treatment systems. The invention solves this problem too.

It should be noted here that PROCERA® is an extensive system with a worldwide customer base and with large quantities of data passing to and from orderers within the system. Upon connection of occasional customers, it is important to be able to distinguish them in the system in a number of respects, inter alia manufacturing-specific properties, debiting, advertising, etc. The invention solves this problem too.

Solution

The feature which can principally be regarded as characterizing an arrangement according to the invention is that the arrangement, i.e. the advanced arrangement, is designed to cooperate with or be compatible with one or more of the other dental treatment systems available on the market. For this purpose the arrangement must comprise one or more adapter units with the ability to receive and transmit ordering and manufacturing information from/to another system or other systems. In addition, the said information must be of such a character that the ordering and manufacturing principles of the arrangement contribute to product manufacture or partial product manufacture related to respective other dental treatment systems which can cooperate with the arrangement. The word "cooperate" here means that the two systems are compatible so that products or product parts in the other systems can be manufactured in the arrangement.

In embodiments of the inventive concept, the information can be related to important parts of common features in the ordering and/or manufacturing principles which exist for the advanced arrangement, here called the first arrangement, for its own dental treatment system and the arrangement or arrangements (the second arrangement or the second arrangements) for other dental treatment system(s). The first arrangement can be designed to receive query profile data and/or manufacturing data from the respective second arrangement and to convert the said data to the first arrangement's own query profile data and manufacturing data.

In further embodiments, the principles of the first arrangement for manufacturing and quality selection are designed to be able to be changed over to permit manufacture of the products or partial products of the other dental treatment system or systems. The first arrangement can operate with a telephone and/or computer network of the local area network type which in principle forms or is included in a coordinating unit within the arrangement. The respective second arrangement can be connected via one or more modems and one or more remote net servers associated with the second arrangement in question. Products or partial products, e.g. in the form of dental caps, included in or belonging to the other dental treatment system concerned can be selected or manufactured in the first arrangement with differences in terms of content and/or structure or quality compared with the first arrangement's normal content, structure and quality. In the case of products or product parts in the form of ceramics or dental caps made of ceramic powder, these can have a different structure or quality compared with the first arrangement's normally designed caps. The manufacture of the products or partial products can take place under the first arrangement's control or under the respective second arrangement's control.

In one embodiment, the first arrangement comprises a user interface for the customers, i.e both the subscribers and the occasional purchasers or users. Coordinating units which distribute incoming and outgoing measures for production units are connected to the interface. For data handling, a number of databases are used whose contents are updated. The databases include event tables which are data-replicated. The coordinating units and production units operate with host computers and each data content item has a host database and there is therefore a host database for customer registers, in which subscribers and occasional customers can be identified. In the event of a query from new occasional customers, their identity and request are noted, and the customer register or customer register part for occasional customers is registered, with updating of the table in question being carried out, e.g. by insertion, amendment or removal of data. The change to the table is data-replicated to the units concerned through the entire system, which data replication is effected from one unit to the other.

Further embodiments will be evident from the attached subclaims.

ADVANTAGES

A number of advantages are afforded by what has been proposed above. The resources of the advanced system can be used for customers and subscribers outside the advanced system's own customer base. The structure and function of the advanced system can be given a greater basis in respect of its development and its information content. By means of the invention, it is also possible to provide coordinated debiting functions for debiting of outside use. Any differences in product design between the various dental treatment systems are eliminated according to the invention so that outside users can use at least essential parts of the advanced system's knowledge and techniques. In addition, for example, one manufacturer's ceramic caps can be replaced by a second manufacturer's ceramic caps (or another dental product) despite the fact that the manufacture takes place in the first arrangement or the first dental treatment system.

DESCRIPTION OF THE FIGURES

A presently proposed embodiment of the novel arrangement having the characteristic features of the invention will now be described with reference to the attached drawings, in which.

DETAILED EMBODIMENT

Figure 1:
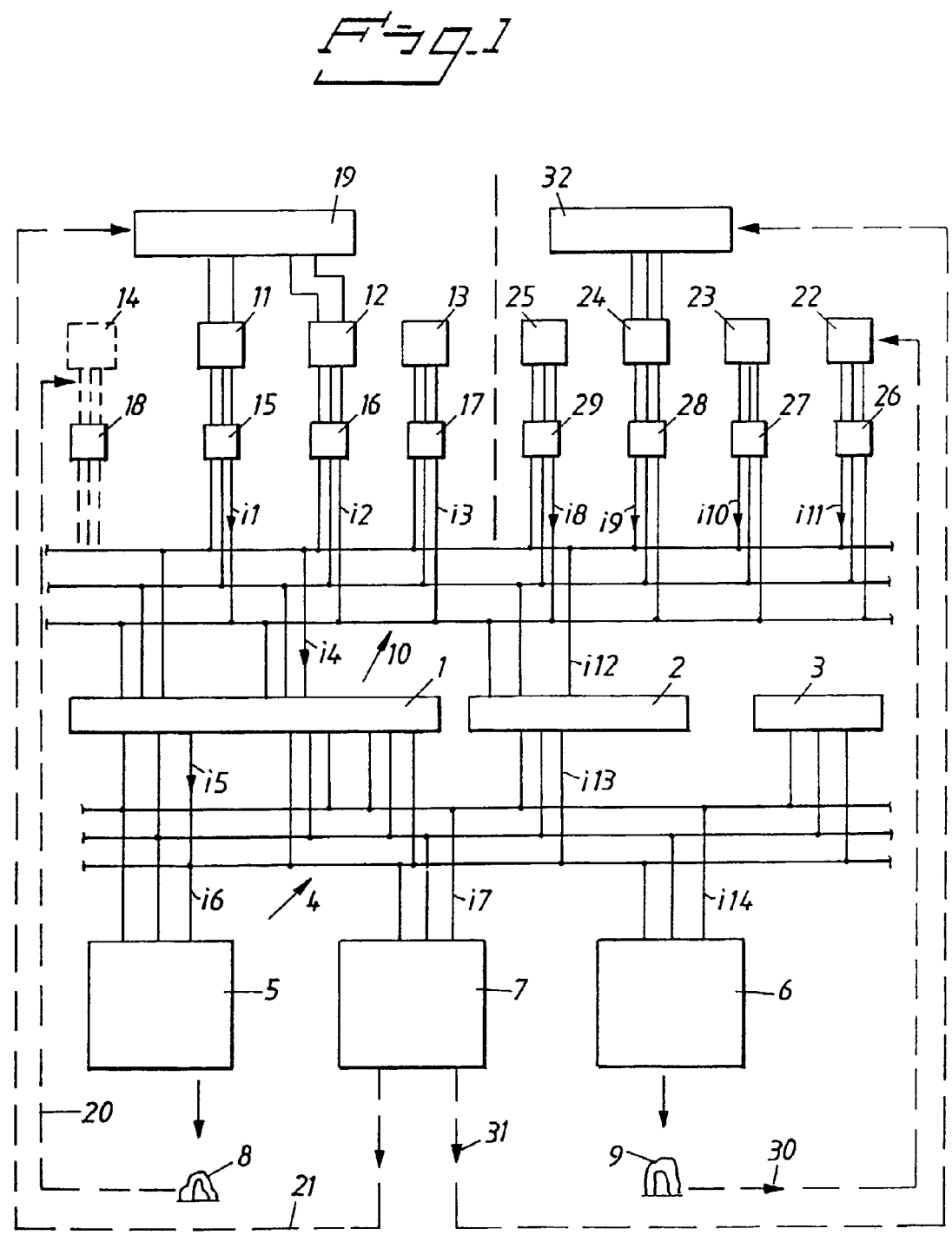
FIG. 1 is a block circuit diagram showing the possible uses, for outside customers, of an advanced dental treatment system.

In FIG. 1, a dental treatment system, e.g. the PROCERA® dental treatment system, is represented by receiving and coordinating units 1, 2, 3 and an internal local network (e.g. LAN) 4 which can be constructed as a telephone/computer network. The system also includes one or more manufacturing units and one or more information-transmitting units 7 for dental products 8, 9 or partial products which can be produced in the system and which the system can send or provide details of.

The dental treatment system 1-7 is connected to an external communications system 10 which can comprise the public telephone and/or computer network system (e.g. comprising the Internet and/or the so-called IBM network) with wire-based and/or mobile-based communication. The data treatment system 1-7 can be seen as a first arrangement for manufacture of dental products or partial products in the generally known BRANEMARK® system. In FIG. 1, the first arrangement's customers are indicated by 11, 12, 13, 14 and can comprise dentists and/or dental technicians who are connected via modem/modem equipment 15, 16, 17 and 18, respectively. The customers 11-14 subscribe to the system or the arrangement 1-7 are for this purpose linked to the system in one way or another. The customers can subscribe to a greater or lesser extent to the services provided by the arrangement. The customers can therefore order products 8 or partial products or can order certain production-specific functions in the arrangement and can carry out the production using their own production equipment/control, etc. In the figure, reference number 19 indicates a customer-related production unit to which the customers 11, 12 are linked.

The ordering of a service or product in the arrangement can be carried out in a known manner (see patent referred to above). Thus, the customer 13 can link up to the net 10 via his modem 17 and can connect to the arrangement 1-7 for ordering the product 8 which is manufactured in the arrangement and is returned physically to the customer via a symbolically indicated connection 20 which leads from the manufacturing unit 8 back to the customer. Thus, for example, the customer 11 can link up in a corresponding way to the arrangement 1-7 via his modem 15 and can request support for his own product manufacture, which support is obtained from or via the unit 7 and is transmitted from this unit to the customer's manufacturing unit 19 via a symbolically indicated connection 21. Alternatively, this last-mentioned connection can be effected in reverse in the system, i.e. via the local network 4, the unit 1, the communications system 10 and the modem 15 to the customer 11. The said order from the customer 13 is effected via the modem 17, the system 10, the units 1 and 5. The said order from the customer 15 is effected via the modem 15, the network 10 and the units 1 and 7.

According to the invention, customers 22, 23, 24 and 25 who are not linked to the first arrangement and who represent a first dental treatment system must be able to use the features and contents of the first arrangement. Access for the outside customers can be made to the public network 10 via modems 26, 27, 28 and 29, respectively. The customers 22 and 23 can be assumed to belong to or be linked to a second dental treatment system which differs from the abovementioned first dental treatment system with customers 11-14. The customers 24, 25 can be assumed to belong to or use a third dental treatment system, etc. The first arrangement comprises a user interface to which coordinating units are connected for the purpose, inter alia, of distinguishing between system subscribers and occasional customers.

The receiving unit or coordinating unit 2 for these customers is connected or can be connected to the network 10. This unit 2 can be regarded as functioning as an adapter unit whose task is to compare the principal conditions and differences in the product design and the information transmission between the different dental treatment systems. This comparison can be made with the aid of previously stored information which is representative of the two compared products/information items. Alternatively, the information items received from the customers can be compared in real time with information items/details which are characteristic of the system/arrangement. Such information items can include product technical data and quality-related information. On the basis of this comparison, the adapter unit will on the one hand be able to report to the outside customer to what extent the customer's wishes can be met, and, on the other hand, give directions to the system so that any differences in production or information transmission can be eliminated. This means, for example, that production of a ceramic crown can be done using the same production method, but with another material composition giving a quality difference comparable with the compared dental treatment systems. In the event of any differences being found, the unit 2 can control the production unit 6 and/or the information-transmitting unit 7 for product/partial product 9 or information from the unit 7. A physical return connection for the product/partial product is indicated by 30. The return route for information transmission from the unit 7 to outside customers 22-25 is symbolized by 31 and can alternatively take place from the unit 7 to the unit 2 and the relevant modem of the modems 26-29 and the relevant customer of the customers 22-25, to a manufacturing apparatus 32 to which one or more of the customers 22-25 are connected. The described function for the unit 2 can in principle be included in whole or in part in the unit 1 or shared with the unit 3. The functions for the unit 3 can be implemented in a known manner. The system uses a number of databases which are event-updated. In addition, there are host computers for the coordinating units and production units. The host computers operate with host databases and the host computer(s) for the coordinating unit(s) has/have one or more host databases for customer registers which can be divided into subscriber registers and registers for occasional customers.

Figure 2:
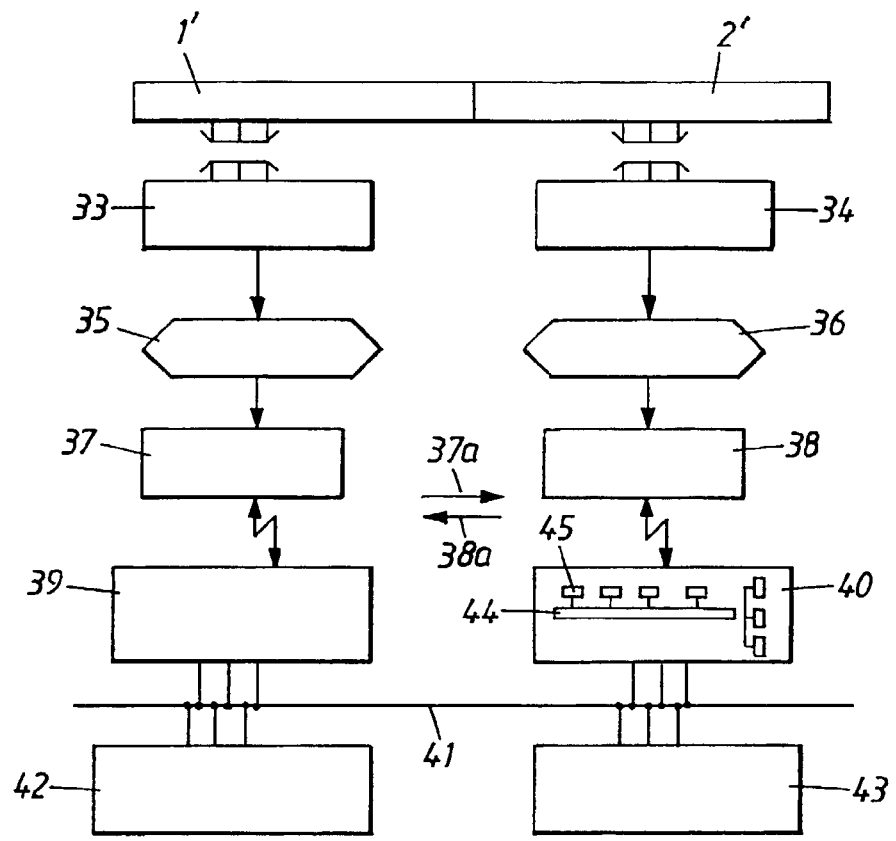
FIG. 2 is a block circuit diagram showing the units included in the arrangement according to FIG. 1.

In FIG. 2, the flow of information from the system's own customers and from the outside customers is received in the units 1' and 2', respectively. The flow of information can relate to titanium crowns, ceramic crowns, bridges, statistics, programs, etc. The information items can relate to scanning functions 33 and 34 which are represented by event tables and interpreted by programs 35 and 36, respectively. Comparison functions 37 and 38 are activated in accordance with the arrows 37a and 38a, and coordinating units or administration units 39, 40 receive and process/distribute the information items via an internal computer network. The units 1', 2' and 22-38 can be placed in locations geographically separate from the units 39 and 40 which, together with additional such units 42 and 43, can administer a large quantity of incoming data, i.e. a very large number of customers. Each unit 39, 40, 42 and 43 includes computer-based equipment with internal network 44, data servers and ISDN connections via which the customers are administered.

Figure 3:
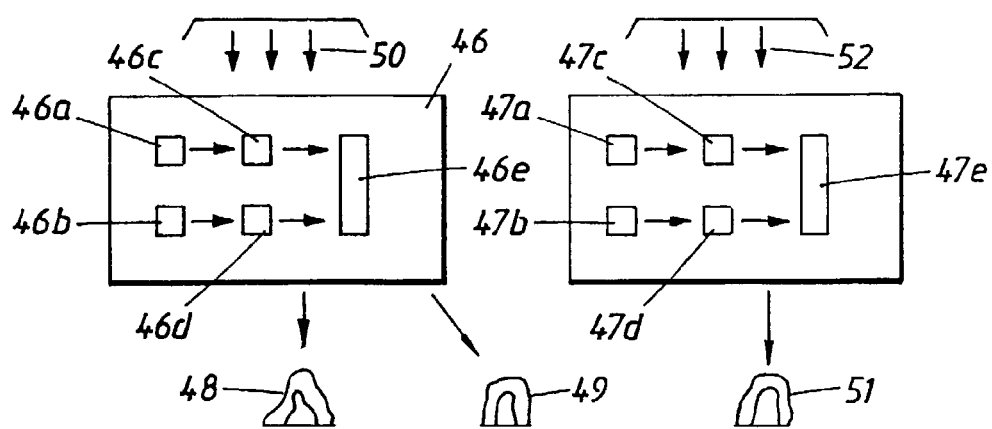
FIG. 3 is a block circuit diagram showing an arrangement for manufacture of dental products.

FIG. 3 shows how manufacturing units 46, 47 can be administered. The manufacturing units can be product-specific and/or customer-specific. Thus, in the unit, ceramic crowns 48 and 49 which are specific to different dental treatment systems can be produced depending on directions 50 from the coordinating units 39, 40 and 42, 43 (see FIG. 2). Selection units are symbolized by 46a and 46b and press and oven functions by 46c, 46d and 46e, respectively. Alternatively, the station 46 can manufacture products or product parts 48 from the actual dental treatment system or arrangement, and the station product or product part 51 as a function of directions 52 from the units 39, 40 and 42, 43 (see FIG. 2) from another dental treatment system or arrangement. The station too has selection functions 47a, 47b and press and oven functions 47c, 47d and 47e, respectively.

The information items according to the above have the following designations. $i_1$-$i_3$ represent information transmission from customers 11-13 to the actual system. $i_4$ represents information items between the network 10 and the unit 1, and $i_5$ and $i_6$ represent information items between the unit 1 and the network 4 and between the network 4 and the unit 5. The signals from the network 4 to the unit 7 are designated $i_7$. Correspondingly, the signals from outside customers are indicated by $i_8$, $i_9$, $i_{10}$ and $i_{11}$. The information items between the network 10, the unit 2 and the unit 6 have the designations $i_{12}$, $i_{13}$ and $i_{14}$. In the case of reversed information transmission, the arrows are directed the other way, i.e. the signals go in the opposite direction from that shown.

The coordinating unit 2 includes debiting function circuits. The network 10 itself can comprise a debiting function for the use of the arrangement 1-7 by the customers 22-25. The debiting systems can be coordinated so that debiting takes place both with respect to time and content. Thus, there is a host database for the debiting function, and the event table in question can thus be updated with respect to date, action, cost, etc., and spread by serial data replication to relevant units in the system. The host database for customer registers can be updated with occasional customer, date, requested action, etc. The updated table is forwarded to the relevant units in the system by serial data replication.

The invention is not limited to the embodiment described above and instead can be modified within the scope of the attached patent claims.

The invention claimed is:

1. An arrangement for producing at least a part of a dental product, the arrangement comprising:
    an interface configured to receive and transmit ordering and manufacturing data from a plurality of users of different dental treatment systems;
    at least one coordinating adapter unit configured to receive and transmit the ordering and manufacturing data from the different dental treatment systems, the at least one coordinating adapter unit configured to utilize ordering, manufacturing, and quality operating principles to compare the ordering and manufacturing data from the different dental treatment systems, distinguish products from the different dental treatment systems, and to convert ordering and manufacturing data from at least one of the different dental treatment system to conform to another of the dental treatment systems, thereby permitting the arrangement to cooperate with the different dental treatment systems;
    a communications network configured to permit communication among elements of the system; and production units configured to manufacture the dental product utilizing the converted ordering and manufacturing data.

2. The system according to claim 1, wherein one of the at least one coordinating adapter units comprises a customer interface.

3. The system according to claim 1, further comprising:
a plurality of databases, wherein contents of the databases are exchanged among all databases such that information entered into one of the databases is transmitted to all databases.

4. The system according to claim 3, wherein the databases comprise a customer register database.

5. The system according to claim 1, wherein the at least one coordinating adapter unit is configured to receive production data from a production system of the different dental treatment systems and convert the production data for producing at least a portion of a dental product with a production system of another of the different dental treatment systems.

6. The system according to claim 1, wherein the communications network comprises a public telephone system.

7. The system according to claim 1, wherein the communications network comprises a local area network.

8. The system according to claim 7, wherein the at least one coordinating adapter unit comprises the local area network and wherein another dental treatment system is connected to the local area network with at least one modem and a remote net server/node.

9. The system according to claim 1, wherein the communications network comprises the internet.

10. The system according to claim 1, wherein the communications network comprises a wireless communications network.

11. The system according to claim 1, wherein the at least one coordinating adapter unit is configured to differentiate between occasional customers and system subscribers.

12. The system according to claim 1, wherein the at least one coordinating adapter unit is configured to compare product design of different dental treatment systems, determine additional information required to permit production by the production unit and locate the additional information.

13. The system according to claim 1, wherein different production units are specific to at least one different dental treatment system and different products.

14. The system according to claim 1, wherein the at least one coordinating adapter unit is configured to carry out debit functions associated with the production of the dental units.

15. The system according to claim 1, wherein the dental products comprise ceramic dental caps or crowns.

16. The system according to claim 15, wherein crowns or caps from a first dental system having a different structure and/or quality compared with a second system and the present invention is configured to replace the caps or crowns of the first system with the caps or crowns of the second system.

17. The system according to claim 1, wherein the at least one coordinating adapting unit comprises at least one event table for new customers or occasional customers.

18. The system according to claim 1, wherein the system at least partially controls manufacture of the dental product after receiving at least one of a query and order profile data.

19. The system according to claim 1, wherein exchange of information between the dental treatment system and another dental treatment system is configured to initiate at least partial dental product manufacture by the other dental treatment system and transfer of information from the system to the other dental treatment system for manufacture of the dental product.

20. The system according to claim 1, further comprising:
at least one database configured to register customers, wherein the database is configured to introduce occasional customers for registration.

21. The system according to claim 20, wherein the system links the occasional customers to functions comprising manufacturing, information transmission, and debiting.

22. The system according to claim 1, further comprising:
a debiting system configured to debit use of the system by outside customers.

23. The system according to claim 1, wherein the production units are product specific or customer specific.

24. A method for producing at least a part of a dental product, the method comprising:
receiving ordering and manufacturing data from a plurality of users of different dental treatment systems;
transmitting at least one of the ordering and manufacturing data from the different dental treatment systems to at least one coordinating adapter unit configured to receive and transmit the ordering and manufacturing data;
interpreting and comparing the ordering and manufacturing data from the different dental treatment systems to distinguish products from the different dental treatment systems utilizing ordering, manufacturing, and quality operating principles;
converting ordering and manufacturing data from at least one of the different dental treatment systems to conform to another of the dental treatment systems utilizing the ordering, manufacturing, and quality operating principles;
transmitting the converted ordering and manufacturing data to the production units configured to manufacture the denial product; and
producing at least a part of the dental product with the production units.

25. The method according to claim 24, further comprising:
distinguishing between subscribers and occasional customers.

26. The method according to claim 24, further comprising:
exchanging data among databases to synchronize contents of the databases.

27. The method according to claim 24, further comprising:
debiting users accounts.

* * * * *